US010414816B2

(12) United States Patent
Park et al.

(10) Patent No.: US 10,414,816 B2
(45) Date of Patent: Sep. 17, 2019

(54) METHOD FOR PURIFYING IMMUNOGLOBULIN (71) Applicant: GREEN CROSS HOLDINGS CORPORATION, Gyeonggi-do (KR)

(72) Inventors: Dong-Hwarn Park, Gyeonggi-do (KR); Ki-Hwan Son, Chungcheongbuk-do (KR); Kang Yun Seo, Gyeonggi-do (KR); Sung Min Choi, Gyeonggi-do (KR); Gun Sul Lee, Gyeonggi-do (KR); Ki-Yong Kim, Gyeonggi-do (KR)

(73) Assignee: GREEN CROSS HOLDINGS CORPORATION, Gyeonggi-Do (KR)

( * ) Notice: Subject to any disclaimer, the term of this patent is extended or adjusted under 35 U.S.C. 154(b) by 332 days.

(21) Appl. No.: 15/123,925

(22) PCT Filed: Mar. 11, 2014

(86) PCT No.: PCT/KR2014/002021
§ 371 (c)(1),
(2) Date: Sep. 6, 2016

(87) PCT Pub. No.: WO2015/137531
PCT Pub. Date: Sep. 17, 2015

(65) Prior Publication Data
US 2017/0015732 A1    Jan. 19, 2017

(51) Int. Cl.
*C07K 16/06*    (2006.01)
*C07K 1/36*    (2006.01)

(52) U.S. Cl.
CPC .............. *C07K 16/065* (2013.01); *C07K 1/36* (2013.01)

(58) Field of Classification Search
None
See application file for complete search history.

(56) References Cited

U.S. PATENT DOCUMENTS

| | | | |
|---|---|---|---|
| 4,124,576 A | 11/1978 | Coval | |
| 4,764,369 A | 8/1988 | Neurath et al. | |
| 6,124,437 A * | 9/2000 | Hirao | C07K 16/065 424/85.5 |
| 9,023,994 B2 * | 5/2015 | Mintz | C07K 16/065 424/130.1 |
| 2001/0051708 A1 * | 12/2001 | Laursen | A61K 39/39591 530/387.1 |
| 2002/0177693 A1 | 11/2002 | Lebing et al. | |
| 2006/0194953 A1 * | 8/2006 | Bonnerjea | C07K 1/22 530/387.1 |
| 2007/0173638 A1 | 7/2007 | Buchacher et al. | |
| 2011/0014203 A1 * | 1/2011 | Nilsson | A61K 9/0019 424/142.1 |
| 2013/0058961 A1 | 3/2013 | Teschner et al. | |
| 2013/0317457 A1 * | 11/2013 | Schmitt | A61F 9/0008 604/290 |
| 2014/0116941 A1 * | 5/2014 | Thorm | B01D 61/145 210/635 |
| 2016/0368970 A1 * | 12/2016 | El Menyawi | C07K 1/30 |

(Continued)

FOREIGN PATENT DOCUMENTS

DE    2604759 A1    9/1977
KR    10-1983-0007083 B1    12/1983
(Continued)

OTHER PUBLICATIONS

Schreiner, Abstract 620 "Stabilty of a new liquid intravenous immunoglobulin preparation (IGIV-C 10%) Manufactured using a novel production process" 2003; p. S224 (Year: 2003).*
PALL Life Sciences Product Note USD 2774 "Q, S. Deae, CM ceramic HyperD F ion excchange sorbents" pp. 1-6 (Year: 2011).*
Cohn, E.J., et al., "Preparation and Properties of Serum and Plasma Proteins. IV. A System for the Separation into Fractions of the Protein and Lipoprotein Components of Biological Tissues and Fluids", "Journal of the American Chemical Society", Mar. 1, 1946, pp. 459-475, vol. 68.

(Continued)

Primary Examiner — Daniel E Kolker
Assistant Examiner — James L Rogers
(74) Attorney, Agent, or Firm — Hultquist, PLLC; Steven J. Hultquist (57)    ABSTRACT The present invention relates to a method for purifying an immunoglobulin, and more particularly, to a method for purifying an immunoglobulin, which comprises: dissolving immunoglobulin-containing plasma protein fraction I+II+III or fraction II+III; adding caprylate to the solution to cause precipitation; performing dialysis and concentration after removal of the precipitate; performing anion exchange resin and ceramic cation exchange resin purification processes to effectively remove a solvent and detergent added to inactivate viruses; and performing elution while maintaining salt concentration at a constant level to maintain the immunoglobulin polymer content at a low level. According to the method for preparing the intravenous immunoglobulin according to the present invention, a precipitation step of preparing fraction II from fraction I+II+III or fraction II+III as a starting material can be omitted, and problems, including a complicated process and a low yield, which occur in the conventional preparation process employing the polyethylene glycol treatment process, can be solved by use of first sodium caprylate precipitation, anion exchange chromatography and cation exchange chromatography. In addition, when the immunoglobulin purification method according to the present invention is used, the efficiency with which impurities and thrombotic substances are removed can be increased and the immunoglobulin polymer content can be maintained, and thus a stable immunoglobulin with increased quality can be produced.

17 Claims, 3 Drawing Sheets

(56) References Cited

U.S. PATENT DOCUMENTS

| | | | |
|---|---|---|---|
| 2017/0022248 A1* | 1/2017 | Son | C07K 1/36 |
| 2017/0218051 A1* | 8/2017 | Gnauer | C07K 16/18 |
| 2018/0140699 A1* | 5/2018 | Shin | A61K 39/395 |

FOREIGN PATENT DOCUMENTS

| | | | |
|---|---|---|---|
| KR | 10-2010-0028064 A | 3/2010 | |
| KR | 10-2012-0107140 A | 9/2012 | |
| KR | 10-1206788 B1 | 11/2012 | |
| WO | WO-9518155 A1 * | 7/1995 | C07K 16/065 |
| WO | WO2000076534 A1 | 12/2000 | |
| WO | WO-2005073252 A1 * | 8/2005 | A61L 2/0011 |

OTHER PUBLICATIONS

Kistler, P., et al., "Large Scale Production of Human Plasma Fractions", "Vox Sanguinis", Jul. 8, 1962, pp. 414-424, vol. 7.

Polson, A., et al., "The Fractionation of Protein Mixtures by Linear Polymers of High Molecular Weight", "Biochimica et Biophysica Acta", 1964, pp. 463-475, vol. 82.

Polson, A., et al., "Fractionation of Plasma with Polyethylene Glycol", "Vox Sanguinis", Jul. 8, 1972, pp. 107-118, vol. 23.

* cited by examiner

1 Cohn fraction I + II + III paste
2 Caprylate precipitation
3 First anion exchange chromatography (loading)
4 First anion exchange chromatography (passed liquid)
5 First anion exchange chromatography (elution)
6 Cation exchange chromatography (loading)
7 Cation exchange chromatography (washing)
8 Cation exchange chromatography (elution)
9 Second anion exchange chromatography (loading)
10 Second anion exchange chromatography (passed liquid)
11 Second anion exchange chromatography (elution)
12 Nanofiltration
13 Concentration
14 Crude solution
15 Internal control

METHOD FOR PURIFYING IMMUNOGLOBULIN

CROSS-REFERENCE TO RELATED APPLICATION

This application is a U.S. national phase application under the provisions of 35 U.S.C. § 371 of International Patent Application No. PCT/KR14/02021 filed Mar. 11, 2014. The disclosure of such international patent application is hereby incorporated herein by reference in its entirety, for all purposes.

TECHNICAL FIELD

The present invention relates to a method for purifying an immunoglobulin, and more particularly, to a method for purifying an immunoglobulin, which comprises: dissolving immunoglobulin-containing plasma protein fraction I+II+III or fraction II+III followed by performing a precipitation reaction by adding caprylate, performing dialysis and concentration, and then effectively removing a solvent and detergent added to inactivate viruses by subjecting to anion exchange resin and ceramic cation exchange resin purification processes, and maintaining salt concentration at a constant level to maintain the immunoglobulin polymer content at a low level.

BACKGROUND ART

Immunoglobulins that are plasma proteins containing antibodies against various viruses and bacteria are used as drugs to prevent or treat diseases by administration to either subjects who naturally lack antibodies or patients who are in need of artificial supplement of antibodies because of viral or bacterial diseases.

In order to use such immunoglobulins as drugs, immunoglobulins for subcutaneous or intramuscular injection have been prepared according to the cold ethanol fractionation process (Cohn E. et al., *J. Am. Chem. Soc.,* 68:459, 1946) developed by Cohn and Oncley or the modified cold ethanol fractionation process (Kistler P, Nitschmann H S, *Vox Sang,* 7:414. 1952) developed by Kistler and Nitschmann.

However, immunoglobulins for intramuscular injection have the following problems: 1) the doses of such immunoglobulins are limited, making it impossible to administer the immunoglobulins in large amounts; 2) the immunoglobulins cause pain at the site injected with the immunoglobulins; 3) the immunoglobulins have a low content of natural immunoglobulin G (IgG) having antibody activity; 4) the antibody activity of the immunoglobulins is reduced by protease at the injected site; and 5) the time taken to reach peak plasma concentrations is 24 hours or more.

In order to solve the problems of intramuscular injection, administration of immunoglobulins by intravenous injection was attempted. However, when immunoglobulin preparations were administered intravenously, a variety of immediate side effects, including difficult breathing and circulatory system shock, appeared due to a serious side effect (anaphylactic reaction) attributable to aggregates with anti-complementary activity. Such symptoms appeared mainly in immunoglobulin-deficient patients. Particularly, a side effect of serious hypersensitivity was observed in patients in which anti-IgA antibodies appeared.

Thus, as intravenous injection of immunoglobulins is impossible due to the above-described problems, development of immunoglobulin preparations for intravenous injection has been required, and methods capable of removing the above-described aggregates and/or preventing aggregate formation during preparation processes have been developed. Intravenous injection of immunoglobulins has become possible as a result of treating immunoglobulins with proteases such as pepsin, papain or Plasmin, or chemical substances such as β-propiolactone, to change their structure so as to suppress the formation of immunoglobulin aggregates or destroy immunoglobulin aggregates, thereby reducing the anti-complementary activities of the immunoglobulins.

The first-generation intravenous immunoglobulin (IVIG) products were prepared by treating a starting material (Cohn fraction II) with pepsin to remove immunoglobulin aggregates. The preparation process did not comprise a column chromatography step, and the prepared product was lyophilized so as to be stably maintained over a suitable period of time, and was dissolved immediately before use. However, it was found that IVIG products manufactured by some manufacturers caused viral infections such as viral hepatitis C. For this reason, one or more steps of inactivating and/or removing known virus were added to the preparation process. Thereafter, the second-generation IVIG products with low anti-complementary activity and higher stability were disclosed in the mid-1980s, and the IVIG products were purified by several chromatography steps.

Such preparations were injected intravenously, and thus overcame the disadvantages of intramuscular immunoglobulins, including limited dose, pain at the injected site, and the reduction in antibody activity of immunoglobulins by protease, and the time taken to reach peak plasma concentrations was also reduced to several hours or less.

However, the intravenous immunoglobulin products as described above have little or no natural IgG with antibody activity due to their structural change, and thus have reduced or no complement binding ability and also have a blood half-life as short as about 4-12 days, suggesting that they exhibit no satisfactory effects on the prevention and treatment of diseases. Furthermore, the first-generation and second-generation IVIG products prepared in the form of lyophilized powder require an additional process for dissolving them, and have low dissolution rates. For this reason, liquid IVIG products have been developed, and improved processes have been required to obtain more stable and pure IVIG products.

In connection with this, German Patent No. 2,604,759 and U.S. Pat. No. 4,124,576 discloses methods of obtaining pure IgG (third-generation IVIG) with antibody activity by using a non-ionic surfactant such as polyethylene glycol, unlike the above-described gamma-immunoglobulin for intravenous injection. Such IgG preparations have complement binding ability and increased blood half-lives, and thus can show good effects on the prevention and treatment of diseases. However, these preparations produced by treatment with polyethylene glycol can still cause side effects, because it is difficult to completely remove aggregates with anti-complementary activity from these preparations (showing an anti-complementary activity of about 0.02 U/mg).

In addition, Korean Laid-Open Publication No. 1983-0007083 discloses a method of preparing an intravenous immunoglobulin from Cohn fraction II or fraction II+III, isolated from human plasma, by treatment with polyethylene glycol. However, there are problems in that the process is complicated and the yield is low.

Accordingly, the present inventors have made extensive efforts to solve the above-described problems occurring in the prior art, and as a result, have found that, when an immunoglobulin is purified from immunoglobulin-containing plasma protein fraction I+II+III or fraction II+III as a starting material by sodium caprylate precipitation, anion exchange chromatography and cation exchange chromatography, problems, including a complicated process and a low yield, which occur in conventional preparation methods employing polyethylene glycol treatment, can be solved, and a precipitation I+III step for preparing fraction II and a precipitation II step can be omitted so that a process for producing an intravenous immunoglobulin preparation is very easily performed, thereby completing the present invention.

DISCLOSURE OF INVENTION

Technical Problem

It is an object of the present invention to provide a method for purifying immunoglobulins, which can efficiently remove impurities and thrombotic substances in order to produce a stable and high-purity immunoglobulin.

Technical Solution

To achieve the above object, the present invention provides a method for purifying an immunoglobulin, comprising the steps of:

(a) dissolving immunoglobulin-containing plasma protein fraction I+II+III or fraction II+III, followed by performing a precipitation reaction by adding a precipitant;

(b) removing a precipitate produced from (a), followed by filtering a supernatant comprising immunoglobulin, concentrating a filtrate, subjecting a concentrate to an anion exchange chromatography, and recovering a fraction not attached to column of the anion exchange chromatography;

(c) treating the recovered fraction with a solvent/detergent to inactivate viruses, followed by subjecting the fraction to cation exchange chromatography to remove the solvent/detergent;

(d) dialyzing and/or concentrating an eluate obtained from the cation exchange chromatography, subjecting the eluate to anion exchange chromatography, and recovering a fraction not attached to column of the anion-exchange chromatography; and (e) filtering the recovered fraction through a virus filter, and dialyzing and/or concentrating the filtrate, thereby obtaining a purified immunoglobulin.

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods, which will be described below, are those well known and commonly employed in the art.

As used herein, the expression "immunoglobulin-containing plasma protein" is meant to encompass cryoprecipitate-free plasma obtained by removing various plasma proteins such as Factor IX and antithrombin from human plasma or human placental plasma, various Cohn fractions, and fractions obtained by ammonium sulfate or PEG (Polson et al., *Biochem Biophys Acta*, 82:463, 1964); Polson and Ruiz-Bravo, *Vox Sang*, 23:107. 1972) precipitation. Preferably, the plasma protein fraction that is used in the present invention may be Cohn fraction II, Cohn fraction I+II+III or Cohn fraction II+III.

In the present invention, fraction I+II+III or fraction II+III obtained from human plasma according to a conventional Cohn plasma fraction method was used. A subsequent purification process for removing various lipoproteins, fibrinogens, α-globulin, β-globulin and various coagulation factors from I+II+III or fraction II+III was performed.

In the present invention, the human plasma used was FDA-approved American plasma subjected to Biotests, including nucleic acid amplification tests on human immunodeficiency virus (HIV), hepatitis C virus (HCV), hepatitis B virus (HBV) and parvovirus B19, and serological tests. The plasma stored at −20° C. or below was thawed by incubation in a jacketed vessel at 1 to 6° C. for 12-72 hours.

While the plasma was thawed under the above-described conditions, a cryoprecipitate including fibrinogen and coagulation factors was produced. The produced cryoprecipitate was removed by centrifugation, and the remaining cryo-poor plasma was recovered. Then, precipitation and filtration processes were repeated, thereby obtaining fraction I+II+III.

In the filtration process for isolating immunoglobulin-containing plasma, a filter aid was added to and mixed with the cryo-poor plasma which was then separated into a supernatant and a precipitate by means of a filter press. As the filter aid, Celpure 300 or Celpure 1000 was used.

In the method of the present invention, dissolution of fraction I+II+III or fraction II+III in step (a) is performed by adding distilled water to the fraction such that the ratio of fraction I+II+III or fraction II+III:distilled water is 1:6 to 1:10, and the distilled water may be distilled water for injection.

The plasma protein fraction is preferably suspended (dissolved) in water and/or buffer at a substantially non-denaturing temperature and pH. The term "substantially non-denaturing" implies that the condition to which the term refers does not cause substantial irreversible loss of functional activity of the IgG molecules, e.g. loss of antigen binding activity and/or loss of biological Fc-function.

Advantageously, the plasma protein fraction is dissolved in water acidified with at least one non-denaturing buffer at volumes of from 6 to 10, preferably from 7 to 8, times that of the plasma protein fraction. The pH of the immunoglobulin-containing suspension is preferably maintained at a pH below 6, such as within the range of 4.0-6.0, preferably 4.1-4.3, in order to ensure optimal solubility of the immunoglobulin. Any acidic buffer known in the art can be used, but sodium phosphate, sodium acetate, acetic acid, hydrochloric acid, or water (distilled water) may preferably used as the acidic buffer. In the present invention, distilled water or distilled water for injection was used.

In the present invention, step (a) is a step of isolating an immunoglobulin-containing supernatant from other substances by precipitation.

The precipitant that is used in the present invention may be at least one selected from among various molecular weight forms of polyethylene glycol (PEG), caprylic acid and ammonium sulfate. A non-denaturing water-soluble protein precipitant may be used as alternative means for the precipitation. Preferably, caprylic acid may be used.

Formation of the precipitate in step (a) is performed by adding the precipitant at a concentration of 5-26 mM, preferably 19-21 mM, and then adjusting the pH of the solution to 4.0-6.0, preferably 4.5-5.5. Adjustment of the pH may be performed by adding acetic acid or sodium hydroxide, but is not limited thereto. It will be obvious to those skilled in the art that other substances that can generally be used for pH adjustment may be used in the present invention.

The precipitation by addition of the precipitant is performed for about 1 hour, preferably 50 minutes to 1 hour and 10 minutes, until equilibrium is reached between the solid phase and the liquid phase. Throughout the precipitation, the suspension is maintained at a low temperature, preferably 2 to 6° C., and the most suitable temperature depends on the identity of the protein precipitant.

The precipitate formed by precipitation contains large amounts of aggregated protein material, and the supernatant contains an immunoglobulin, and thus only the supernatant may be collected to purify the immunoglobulin. The immunoglobulin-containing supernatant may additionally be filtered in order to remove, for example, large aggregates, filter aid, and residual non-dissolved paste. The filtration is preferably performed by means of depth filters, for example, C150 AF, AF 2000 or AF 1000 (Schenk), 30LA (Cuno) or similar filters. In some cases, the removal of aggregates, filter aid, and residual non-dissolved protein material can also be carried out by centrifugation.

In the present invention, in order to extract an immunoglobulin from fraction I+II+III paste, distilled water or WFI (distilled water for injection) was added such that the ratio of fraction I+II+III paste:distilled water would be 1:6 to 10 and the concentration of extracted protein would be 15 mg/ml. The pH of the solution was adjusted to 4.2±0.1 using 1M acetic acid, followed by extraction of fraction I+II+III paste.

A 1M sodium caprylate solution was added to the extract such that the concentration of caprylate would be 20±1.0 mM, and then the extract solution was adjusted to a pH of 5.1±0.1 using 1M acetic acid or 0.5M sodium hydroxide (NaOH), and subjected to precipitation at 4° C. for 1 hour±10 minutes. The supernatant was recovered and filtered through a depth filter to obtain an immunoglobulin solution.

In the present invention, step (b) is a step of concentrating the immunoglobulin and removing impurities. In this step, the concentration of the immunoglobulin is controlled to 10-50 mg/ml, preferably 20-30 mg/ml, and anion exchange chromatography is performed at a pH of 5.0-6.0 and a flow rate of 95-145 cm/hr. A fraction not attached to the column used to perform the anion exchange chromatography is recovered with 1.6-2.0 loading volumes (LV). Preferably, the pH is adjusted to 5.4-5.8, more preferably 5.5-5.7.

The concentrated immunoglobulin-containing solution may be subjected to anion or cation exchange chromatography in one or more steps in order to remove the precipitant and other plasma proteins including immunoglobulin A (IgA), albumin and aggregates. In the present invention, anion exchange chromatography was performed to remove caprylate and other plasma proteins from the concentrated immunoglobulin-containing solution.

The anion exchange resin that is used in the anion-exchange chromatography step may be one substituted with diethylaminoethyl (DEAE) or quaternary ammonium groups, but is not limited thereto. Preferably, the anion exchange resin may be any one selected from among anion exchange resins having a strongly basic quaternary ammonium group or a weakly basic diethylaminoethyl (DEAE) group.

For example, as a strongly basic anion exchange resin, Q Sepharose Fast Flow, Q Sepharose High Performance, Resource Q, Source 15Q, Source 30Q, Mono Q, Mini Q, Capto Q, Capto Q ImpRes, Q HyperCel, Q Cermic HyperD F, Nuvia Q, UNOsphere Q, Macro-Prep High Q, Macro-Prep 25 Q, Fractogel EMD TMAE(S), Fractogel EMD TMAE Hicap (M), Fractogel EMD TMAE (M), Eshmono Q, Toyopearl QAE-550C, Toyopearl SuperQ-650C, Toyopearl GigaCap Q-650M, Toyopearl Q-600C AR, Toyopearl SuperQ-650M, Toyopearl SuperQ-650S, TSKgel SuperQ-5PW (30), TSKgel SuperQ-5PW (20), TSKgel SuperQ-5PW or the like may be used, but is not limited thereto, and any anion exchange resin known in the art may be used.

The appropriate volume of resin used in the anion exchange chromatography is reflected by the dimensions of the column, i.e., the diameter of the column and the height of the resin, and varies depending on, for example, the amount of the immunoglobulin in the applied solution and the binding capacity of the resin used. Before performing anion exchange chromatography, the anion exchange resin is preferably equilibrated with a buffer which allows the resin to bind its counterions.

In the present invention, the anion exchange resin used is Q Sepharose Fast Flow, and the column buffers used may be equilibration buffer known in the art, for example, sodium phosphate buffer, citrate buffer, acetate buffer or the like, wash buffer and elution buffer.

The column for anion exchange chromatography was loaded with 25±0.5 mM sodium acetate (NaOAc) buffer such that the pH would be 5.6±0.1, and the flow rate of the mobile phase was adjusted to 120±25 cm/hr. The concentrated immunoglobulin solution was loaded into the column in an amount of 90.0±20 mg/mL.

In the present invention, step (c) is a step of inactivating viruses such as potential lipid enveloped viruses in the immunoglobulin-containing solution and then removing a substance used for the inactivation. In this step, a virus-inactivating agent, preferably a solvent and/or a detergent, may be used. Most preferably, solvent & detergent treatment employing a solvent-detergent mixture may be used.

Through step (c), lipid enveloped viruses (e.g. HIV1 and HIV2, hepatitis type C and non A-B-C, HTLV 1 and 2, the herpes virus family, including CMV and Epstein Barr virus) can be inactivated, and thus the safety of the final product can be increased.

In step (c), any solvent and detergent may be used without limitation, as long as they have the capability to inactivate viruses, particularly lipid enveloped viruses. The detergent may be selected from the group consisting of non-ionic and ionic detergents and is preferably selected to be substantially non-denaturing. Particularly, a non-ionic detergent is preferable in terms of easy removal. The solvent is most preferably tri-n-butyl phosphate (TNBP) as disclosed in U.S. Pat. No. 4,764,369, but is not limited thereto.

The virus-inactivating agent that is used in the present invention is preferably a mixture of TNBP and at least one selected from among polysorbate 80 (Tween 80), Triton X-100 and Triton X-45, but is not limited thereto.

The preferred solvent/detergent mixture is added such that the concentration of TNBP in the immunoglobulin-containing solution is 0.2-0.6 wt %, preferably 0.24-0.36 wt %, and such that the concentration of Tween 80 is 0.8-1.5 wt %, preferably 0.8-1.2 wt %.

The virus-inactivation step is performed under conditions that inactivate enveloped viruses, resulting in a substantially virus-safe immunoglobulin-containing solution. Such conditions include a temperature of 4-30° C., preferably 19-28° C., most preferably 24-26° C., and an incubation time of 1-24 hours, preferably 4-12 hours, most preferably about 8 hours, to ensure sufficient virus inactivation.

In the present invention, the cation-exchange chromatography in step (c) may be performed at a pH of 4.5-5.5 and a flow rate of 110-130 cm/hr. Preferably, the pH is adjusted to 4.9-5.1. The amount of immunoglobulin loaded onto the cation-exchange resin is 90-130 mg per ml of the cation-exchange resin, preferably 95-105 mg per ml of the resin. After adsorption of the immunoglobulin, washing with equilibration buffer is performed. The equilibration buffer that is used in the washing may be used in an amount of at least three column volumes, preferably at least five column volumes. After washing, the immunoglobulin is eluted with at least 8 column volumes of elution buffer.

The cation exchange resin that is used in the present invention may be Sephardex, Sepharose, HyperCell or Source, but is not limited thereto, and other cation exchange resins known in the art may also be used. In the present invention, a ceramic-based cation exchange resin may preferably be used. In an example of the present invention, CM Hyper D gel that is a ceramic-based resin was used as the cation exchange resin, and equilibration buffer known in the art, such as sodium phosphate buffer, citrate buffer or acetate buffer, wash buffer and elution buffer were used as the column buffers.

The elution of the immunoglobulin from the cation exchange resin is performed with a substantially non-denaturing buffer having a pH and ionic strength sufficient to cause efficient elution of the IgG, thereby recovering an immunoglobulin-containing eluate. Herein, "efficient elution" means that at least 75%, such as at least 80%, for example, at least 85%, of the immunoglobulin solution loaded onto the cation exchange resin is eluted from the cation exchange resin.

In the present invention, the cation exchange chromatography in step (c) may be performed at the salt concentration of the eluting buffer, which is sufficiently high to displace the immunoglobulin from the cation exchange resin. It may be performed at a salt concentration of 400-600 mM, preferably 500 mM.

In the present invention, step (d) is a step of further removing impurities.

In order to maintain the content of polymers in dialysis and/or concentration, step (d) is preferably performed in a state in which the salt concentration of the eluate obtained from the cation exchange chromatography column is maintained at 50-150 mM. When an elution method enabling a low salt concentration to be maintained is used in the protein elution step, the polymer content of the immunoglobulin can be minimized, and thus the immunoglobulin with increased quality can be purified. In the present invention, the eluate obtained from the cation exchange resin was maintained at a salt concentration of 100 mM or less in order to maintain the polymer content.

In the present invention, the dialysis and/or concentration in step (d) may be performed using an ultrafiltration/diafiltration (UF/DF) system. It is performed at an osmotic pressure of 10 mOsmol/kg or lower, and then the pH is adjusted to 5.5-6.5. Namely, the eluate from the cation exchange chromatography column is dialyzed and concentrated, and the dialysis and concentration by diafiltration and ultrafiltration, respectively, are performed in one step. The membranes employed for the diafiltration/ultrafiltration advantageously have a nominal weight cutoff within the range of 50,000 Da.

In the present invention, diafiltration was performed in order to remove low-molecular ions from the cation exchange chromatography eluate, and the osmotic pressure in the UF/DF system was maintained at 10 mOsmol/kg or less. It was found that the dialyzed and/or concentrated immunoglobulin was concentrated to 1.5±0.1 as measured by a refractometer (T/S meter).

In the present invention, the anion exchange chromatography in step (d) is performed at a pH of 5.5-6.5 and a flow rate of 90-150 cm/hr, and a fraction not attached to the column used to perform the anion exchange chromatography is recovered with 0.8-1.2 loading volumes (LV). Preferably, the pH may be adjusted to 5.78-6.30, preferably 6.0-6.2, and the fraction not attached to the anion exchange chromatography column may preferably be recovered with 0.96-1.04 loading volumes (LV).

In addition, in step (d), the pH of the fraction not attached to the anion exchange chromatography column may be adjusted to 4.0-5.5, preferably 4.3-4.7, by adding an acid, preferably 1M sulfuric acid, hydrochloric acid or acetic acid.

In the present invention, EMD TMAE (Fractogel EMD TMAE) was used as the anion exchange resin. It was packed into the column, and then equilibrated with 20±1.0 mM sodium acetate (NaOAc) buffer such that the pH would be 6.1±0.05. The flow rate of the mobile phase was adjusted to 120±30 cm/hr. The dialyzed and/or concentrated immunoglobulin solution was loaded into the column in an amount of 110.0±10 mg/mLr, and the fraction not attached to the anion exchange chromatography column was recovered with 1.0±0.04 loading volumes, and then adjusted to a pH of 4.5±0.2 by addition of 1M acetic acid.

In the present invention, the filtration in step (e) may be performed using a nanofiltration or ultrafiltration/diafiltration system. The nanofiltration may be performed at a pressure of 2.0-3.0 bar, and the ultrafiltration/diafiltration may be performed at an osmotic pressure of 10 mOsmol/kg or lower, and then the pH may be adjusted to 4.5-5.5.

The nanofiltration is an important virus-removing step. In this step, the fraction not attached to the second anion exchange chromatography column was filtered through a Pall DVD pre-filter and a DV20 virus filter at a pressure of 2.5±0.5 bar, preferably 2.5±0.2 bar, to remove viruses from the immunoglobulin solution. Then, diafiltration was performed using an ultrafiltration/diafiltration (UF/DF) system at a pressure of 10 mOsmol/kg or less to remove low-molecular ions.

The method of the present invention may further comprise, after step (e), a step of adding a stabilizer to prepare an immunoglobulin for intravenous injection.

In the present invention, a stabilizer that can be added may be at least one selected from among sugar alcohol, maltose, sorbitol, mannose, glucose, trehalose, albumin, lysine, glycine, PEG and Tween 80. Preferably, glycine is used as the stabilizer.

The stabilizer may be added to a concentration of 200-300 mM. After addition of the stabilizer, the pH of the immunoglobulin solution may be adjusted to 4.5-5.5. Preferably, the pH may be adjusted to 4.7-4.9 by adding an acid, preferably sulfuric acid or hydrochloric acid.

In the present invention, for stabilization of the immunoglobulin, glycine was added to the dialyzed and/or concentrated immunoglobulin solution to a final concentration of 250±50 mM and thoroughly mixed, and then the solution was adjusted to a pH of 4.8±0.1 by addition of 0.5N hydrochloric acid, and sterilized using a 0.2 μm filter and stored.

The sterilized immunoglobulin preparation for intravenous injection may be diluted or concentrated such that the concentration of the protein (purified immunoglobulin) is 1-30 wt %. In the present invention, the sterilized immunoglobulin preparation was diluted with WFI or concentrated by ultrafiltration such that the protein concentration would be 40-60 g/l, preferably 45-55 g/l, more preferably 49.5-50.5 g/l. Then, glycine was added to the immunoglobulin solution to a final concentration of 250±50 mM and thoroughly mixed, and hydrochloric acid was added to the immunoglobulin solution to adjust the pH to 4.8±0.1, thereby preparing an intravenous immunoglobulin preparation.

In another aspect, the present invention is directed to an intravenous immunoglobulin prepared according to the preparation method of the present invention.

In an example of the present invention, the purity (thrombin/IgG) of an immunoglobulin solution in each preparation step and the concentration of FXI (human coagulation factor XI) in a filtrate or precipitate in each preparation step were measured. As a result, it could be seen that an immunoglobulin solution with a purity of 99% or higher was purified (FIG. 2) and that the coagulation factor FXI was mostly removed (Table 2 and FIG. 3).

EXAMPLES

Hereinafter, the present invention will be described in further detail with reference to examples. It will be obvious to a person having ordinary skill in the art that these examples are illustrative purposes only and are not to be construed to limit the scope of the present invention. Thus, the substantial scope of the present invention will be defined by the appended claims and equivalents thereof.

Example 1

Preparation of Intravenous Immunoglobulin 1-1: Preparation of Plasma

As plasma, FDA-approved plasma was used which was subjected to Biotests, including nucleic acid amplification tests on human immunodeficiency virus (HIV), hepatitis C virus (HCV), hepatitis B virus (HBV) and parvovirus B19, and serological tests.

In the present invention, the US-derived plasma (Batch No. 600B0491) was used. The plasma was stored at −20° C. or below until use. A bottle containing the plasma was opened with a bottle cutting machine, and the plasma was thawed by incubation in a jacketed vessel at 1-6° C. for 12-72 hours.

While the plasma was thawed under the above-described conditions, a cryoprecipitate containing fibrinogen and coagulation factors was produced. The produced cryoprecipitate was removed by centrifugation, and the remaining cryo-poor plasma was recovered.

1-2: Precipitation I

96% ethanol was added to the cryo-poor plasma recovered in Example 1-1 such that the final ethanol concentration would be 8±0.8% at −3±1° C., and then the pH of the solution was adjusted to a 7.2±0.2 using acetate buffer. Whether the recovery of precipitation I is performed depends on the consumption of a process product. In the present invention, a precipitation I process was carried out, but the removal of a precipitate by centrifugation was not carried out.

1-3: Precipitation II+III and Filtration

After the precipitation I process, a precipitation II+III step was performed in order to further precipitate the immunoglobulin contained in the cryo-poor plasma.

To the cryo-poor plasma subjected to the precipitation I step, 96% ethanol was additionally added such that the final ethanol concentration would be 20±2% at −5±1.0° C. Then, the pH of the solution was adjusted to 6.9±0.1 using acetate buffer.

Next, a filter aid (Celpure 300 or Celpure 1000) was added to the solution in an amount of 0.0284 kg per kg of the plasma and mixed for 30±10 minutes. The mixture was separated into a supernatant and a precipitate on a filter press (device information) in a cold room maintained at a temperature of 2 to 8° C.

The supernatant was named "supernatant I+II+III (or II+III)", and the precipitate was named "fraction I+II+IIIw (or II+IIIw)" (w; wash). Fraction I+II+IIIw (or II+IIIw) was immediately used or was stored at −20° C. or below.

1-4: Extraction of Fraction I+II+III Paste, Caprylate Precipitation, Filtration and Concentration To extract an immunoglobulin from the fraction I+II+III paste obtained in Example 1-3, distilled water or WFI (distilled water for injection) was added to the fraction I+II+III paste such that the ratio of fraction I+II+III paste: distilled water would be 1:6 to 10 and the concentration of the extracted protein would be 15 mg/ml. Next, the solution was adjusted to a pH of 4.2±0.1 by addition of 1M acetic acid, and then the fraction I+II+III paste was extracted at a temperature of 2 to 8° C. for 11±0.5 hours.

A 1M sodium caprylate solution was added to the extract such that the concentration of caprylate would be 20±1.0 mM. Next, the extract solution was adjusted to a pH of 5.1±0.1 by addition of 1M acetic acid or 0.5M sodium hydroxide (NaOH), and subjected to precipitation at 4° C. for 1 hour±10 minutes. Next, the supernatant was recovered, and an immunoglobulin solution was recovered from the supernatant by use of depth filter cartridges (Ahlstrom-924 filter, Ahlstrom-950 filter). The recovered immunoglobulin solution was concentrated to 28±2 mg/ml.

1-5: First Anion Exchange Chromatography

In order to remove caprylate and other plasma proteins from the concentrated immunoglobulin solution obtained in Example 1-4, anion exchange chromatography was performed.

The anion exchange resin Q Sepharose FF (GE Healthcare, Catalog No. 17-0510) was packed into a column, and then equilibrated with equilibration buffer (25±0.5 mM sodium acetate (NaOAc), pH 5.6) such that the pH would be 5.6±0.1. Next, the concentrated immunoglobulin solution obtained in Example 1-4 was loaded into the column in an amount of 90.0±20 mg/mLr at a temperature of 25° C. or above and a flow rate of 120±25 cm/hr. Next, a fraction not attached to the anion exchange chromatography column was recovered with 1.6-2.0 loading volumes (LV).

1-6: Solvent/Detergent Treatment

In order to inactivate potential lipid enveloped viruses in the immunoglobulin-containing solution, a step of treating the immunoglobulin-containing solution with a solvent and a detergent was performed.

First, to adjust the pH of the fraction to 5.0±0.1, acetic acid was added to the fraction not attached to the anion exchange chromatography column and recovered in Example 1-5. Then, tri(n-butyl)-phosphate (TNBP) and polysorbate 80 (Tween 80) were added to the fraction to concentrations of 0.3±0.06% and 1±0.2%, respectively, followed by stirring at 200±50 RPM for 20-30 minutes. In order to whether TNBP and Tween 80 in the solution were uniformly mixed, a portion of the solution was sampled and analyzed. Thereafter, the solution was continuously stirred at 25±1.0° C. and 200±50 RPM for 8 hours.

1-7: Cation Exchange Chromatography

In order to remove TNBP, Tween 80 and other impurities such as coagulation factors from the immunoglobulin solution treated with the solvent/detergent, cation exchange chromatography was performed.

The cation exchange resin CM Hyper D gel (Pall Corporation; Catalog No. 20050) that is a ceramic material was packed into a column, and then equilibrated with equilibration buffer (25±0.5 mM sodium acetate (NaOAc)) such that the pH would be 5.0±0.1. Next, the immunoglobulin solution treated with the solvent/detergent in Example 1-6 was loaded into the column in an amount of 100.0±5 mg/mLr at a temperature of 20±2° C. and a flow rate of 120±10 cm/hr. In addition, after washing with at least 5 column volumes of wash buffer, the immunoglobulin was eluted with at least 8 column volumes of elution buffer (elution buffer composition: 20 mM NaOAc pH 4.5 w/0.5M NaCl).

1-8: Diafiltration

In order to remove low-molecular ions from the cation exchange chromatography eluate, diafiltration was performed.

The eluate obtained in Example 1-7 was diafiltered using an ultrafiltration/diafiltration system (Millipore Pellicon2 (50K)) at an osmotic pressure of 10 mOsmol/kg or lower. In order to maintain the immunoglobulin polymer content, the cation exchange chromatography eluate was added to the calculated dialysate concentrate, and the ultrafiltration/diafiltration (UF/DF) was continuously performed while a sodium chloride concentration of 100 mM or lower was maintained.

1-9: Second Anion Exchange Chromatography

In order to remove a polymer and other plasma proteins from the dialyzed and/or concentrated immunoglobulin solution obtained in Example 1-8, second anion exchange chromatography was performed.

The anion exchange resin Fractogel EMD TMAE (Merck-Millipore, Cat No. 116887) was packed into a column, and then equilibrated with equilibration buffer (20±0.5 mM sodium acetate (NaOAc), pH 6.1) such that the pH would be 6.1±0.1. Next, the concentrated immunoglobulin solution obtained in Example 1-8 was loaded into the column in an amount of 110.0±10 mg/mLr at a temperature of 20±2° C. and a flow rate of 120±30 cm/hr. Thereafter, a fraction not attached to the anion exchange chromatography column was recovered with 1.0±0.04 loading volumes (LV), and then adjusted to a pH of 4.5±0.1 by addition of hydrochloric acid.

1-10: Nanofiltration and Diafiltration

Nanofiltration is an important virus-removing step. The dialyzed/concentrated immunoglobulin solution obtained in Example 1-9 was filtered through a Florodyne II prefilter (AB1DJL7PH4) at a pressure of 2.0±0.5 bar or lower and filtered through a virus filter (DV20, AB3DV207PH4) at a pressure of 2.0±0.5 bar to thereby remove viruses from the immunoglobulin solution.

Next, in order to remove low-molecular ions, the immunoglobulin solution was diafiltered at an osmotic pressure of 10 mOsmol/kg or lower using an ultrafiltration/diafiltration (UF/DF) system.

1-11: Addition of Stabilizer and Preparation of Final Preparation

In order to stabilize the immunoglobulin, glycine was added to the dialyzed and/or concentrated immunoglobulin solution to a final concentration of 250±50 mM and thoroughly mixed, and then the pH of the stabilized immunoglobulin solution was measured, and the immunoglobulin solution was adjusted to a pH of 4.8±0.1 by addition of 0.5N hydrochloric acid. Next, the filtrate was sterilized using a 0.2 µm filter and stored in a stainless steel storage tank.

The resulting immunoglobulin preparation for intravenous injection was diluted with WFI or concentrated by ultrafiltration such that the protein concentration would be 50±0.5 g/l. Next, glycine was added thereto to a final concentration of 250±50 mM and thoroughly mixed. Then, the stabilized immunoglobulin preparation was measured for its pH and adjusted to a pH of 4.8±0.1 by addition of hydrochloric acid.

After pH adjustment, the immunoglobulin preparation was sterilized, and transferred to a packing room to prepare a product which was in turn stored at a temperature of 2-8° C.

Example 2

Measurement of Generated Thrombin/IgG (Thromboembolic Risk) in Immunoglobulin Solution in Each Preparation Step The purity (thrombin/IgG) of the immunoglobulin preparation sampled in each step of Example 1 was measured.

2-1: Experimental Method

In the present invention, the measurement of thromboembolic risk in the immunoglobulin solution in each step of Example 1 was performed in accordance with the Thrombin Generation protocol (CBER Thrombin Generation protocol 01 Experiment (100916)a) provided by the CBER (Center for Biologics Evaluation and Research) that is one of the six affiliated analytical organizations of the FDA.

2-2: Experimental Results

Figure 1:
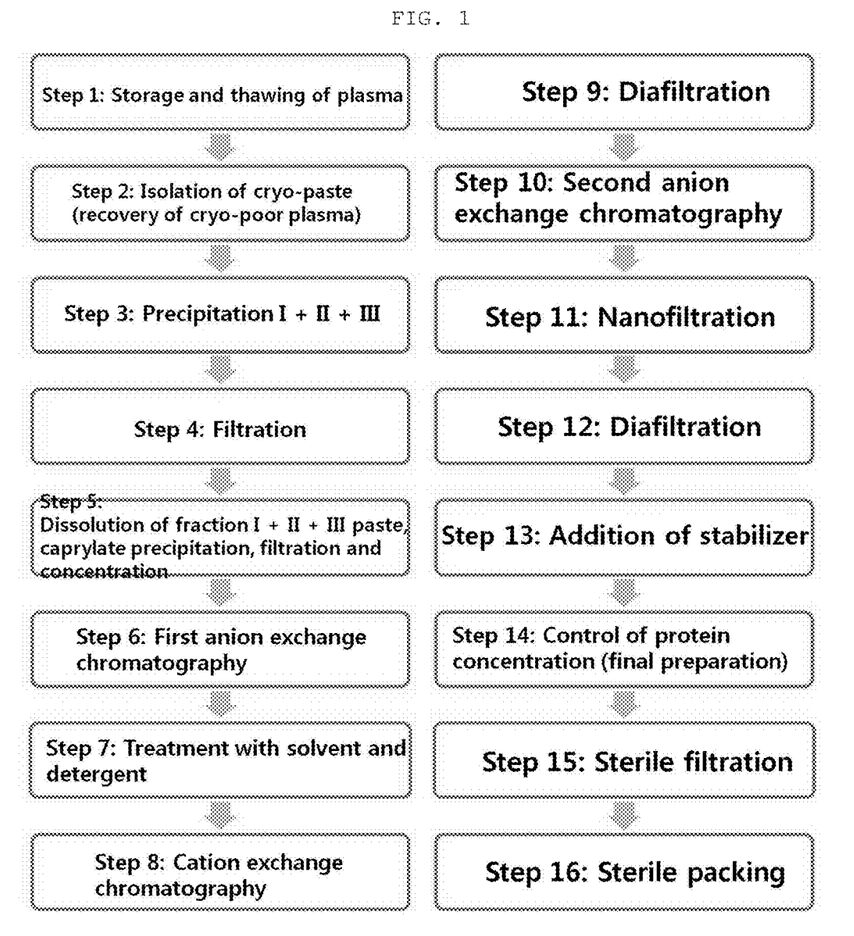
FIG. 1 is a schematic view showing a process for preparing an intravenous immunoglobulin according to the present invention.
Figure 2:
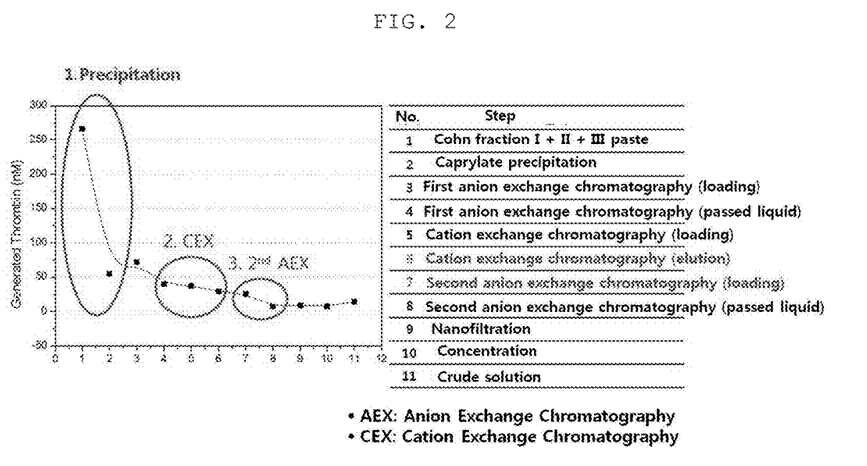
FIG. 2 shows the results of measuring the purity (thrombin/IgG) of an immunoglobulin in each preparation step.
Figure 3:
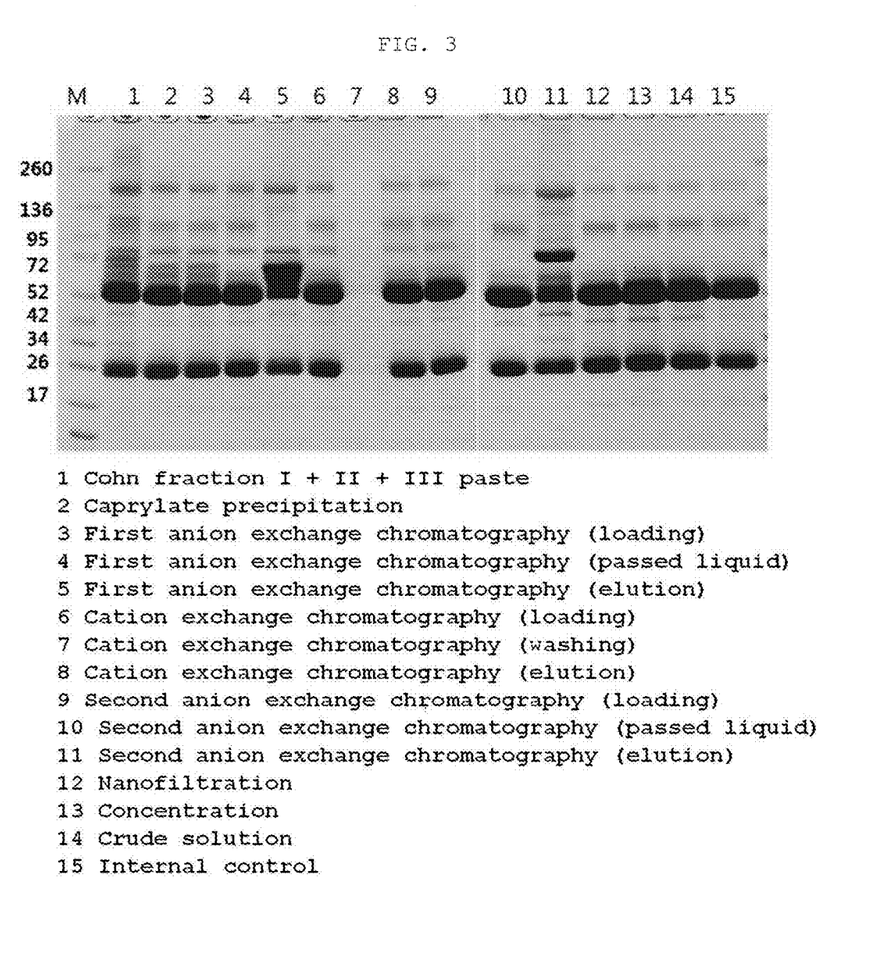
FIG. 3 shows the results of measuring the concentration of FXI (human coagulation factor XI) contained in a filtrate or precipitate in each preparation step by SDS-PAGE.

The immunoglobulin purification process according to the present invention includes the Cohn plasma fractionation method and the ion exchange chromatography purification techniques. As shown in FIG. 2 and Table 1 below, it could be seen that, in the caprylate precipitation process and the cation exchange chromatography and second anion exchange chromatography processes among the chromatographic purification processes, the amount of generated thrombin (that is a thrombotic substance) was effectively reduced.

TABLE 1

Analysis of product in each preparation process

| Processes | Remark | Thrombin (nM) |
|---|---|---|
| 1. Paste extraction | | 266.4 |
| 2. Caprylate precipitation | | 54.9 |
| 3. 1st anion exchange (AEX) chromatography | Loaded portion | 71.9 |
| | Passed portion | 40.0 |
| 4. Cation exchange (CEX) chromatography | Loaded portion | 37.6 |
| | Eluted portion | 29.4 |

TABLE 1-continued

Analysis of product in each preparation process

| Processes | Remark | Thrombin (nM) |
|---|---|---|
| 5. 2nd anion exchange (AEX) chromatography | Loaded portion | 25.5 |
| | Passed portion | 7.4 |
| 6. Nanofilitration | | 9.1 |
| 7. Concentration | | 7.7 |
| 8. Crude solution | | 14.5 |

The results in Table 1 above show that thrombosis that can be caused by intravenous injection of the immunoglobulin can be minimized so that thromboembolism caused by thrombosis can be effectively prevented, thereby maximizing the safety of the immunoglobulin.

Example 3

Measurement of Concentration of FXI (Human Coagulation Factor XI) in Filtrate or Precipitate in Each Preparation Step In order to examine the degree of removal of coagulants, the concentration of FXI (Human Coagulation Factor XI) in the filtrate or precipitate sampled in each preparation step of Example 1 was measured by ELISA (AssayMax Human Factor XI (FXI) ELISA Kit; ssaypro, Catalog No. EF1011-1) and SDS-PAGE.

TABLE 2

FXI contents of purification process products

| | Processes | Remark | FXI (EIA) (ng/mL) |
|---|---|---|---|
| 1 | Paste extraction | | 732.77 |
| 2 | Caprylate precipitation | | 1.76 |
| 3 | 1st anion exchange (AEX) chromatography | Loaded portion | 4.16 |
| 4 | | Passed portion | 1.02 |
| 5 | Cation exchange (CEX) chromatography | Loaded portion | 1.93 |
| 6 | | Eluted portion | 2.16 |
| 7 | 2nd anion exchange (AEX) chromatography | Loaded portion | 0.31 |
| 8 | | Passed portion | 2.67 |
| 9 | Nanofilitration | | 6.46 |
| 10 | Concentration | | 4.89 |
| 11 | Crude solution | | N.D |

The FXI contents of the products of the purification process according to the present invention were measured by ELISA and SDS-PAGE. As a result, it could be seen from Table above and FIG. 3 that the FXI was almost removed in caprylate precipitation, cation exchange chromatography and anion exchange chromatography.

INDUSTRIAL APPLICABILITY

As described above, according to the method for preparing the intravenous immunoglobulin according to the present invention, a precipitation step of preparing fraction II from I+II+III or fraction II+III as a starting material can be omitted, and problems, including a complicated process and a low yield, which occur in the conventional preparation process (polyethylene glycol treatment) employing the polyethylene glycol treatment process, can be solved by use of first sodium caprylate precipitation, anion exchange chromatography and cation exchange chromatography. In addition, when the immunoglobulin purification method according to the present invention is used, the efficiency with which impurities and thrombotic substances are removed can be increased and the immunoglobulin polymer content can be maintained, and thus a stable immunoglobulin with increased quality can be produced.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for purifying an immunoglobulin, comprising the steps of:
    (a) dissolving immunoglobulin-containing plasma protein fraction I+II+III or fraction followed by performing a precipitation reaction by adding a precipitant;
    (b) removing a precipitate produced from (a), followed by filtering a supernatant comprising immunoglobulin, concentrating a filtrate, subjecting a concentrate to an anion exchange chromatography, and recovering a fraction not attached to column of the anion exchange chromatography;
    (c) treating the recovered fraction with a solvent/detergent to inactivate viruses, followed by subjecting the fraction to cation exchange chromatography to remove the solvent/detergent;
    (d) dialyzing and/or concentrating an eluate obtained from the cation exchange chromatography, subjecting the eluate to anion exchange chromatography, and recovering a fraction not attached to column of the anion-exchange chromatography; and
    (e) filtering the recovered fraction through a virus filter, and dialyzing and/or concentrating the filtrate, thereby obtaining a purified immunoglobulin,
    wherein dissolving immunoglobulin-containing plasma protein fraction I+II+III or fraction II+III in step (a) is performed by adding distilled water to the fraction such that the ratio of fraction I+II+III or fraction II+III: distilled water is 1:6 to 1:10,
    wherein the cation exchange chromatography in step (c) is performed at a salt concentration of 400-600 mM and the salt concentration of the eluate obtained from the cation exchange chromatography column in the step (c) is maintained at 50-150 mM in order to maintain the content of polymers during dialysis and/or concentration in step (d).

2. The method of claim 1, wherein the precipitant in step (a) is caprylic acid (caprylate).

3. The method of claim 1, wherein the precipitation reaction in step (a) is performed by adding the precipitant at a concentration of 5-26 mM, and then adjusting the pH of the solution to 4.0-6.0.

4. The method of claim 1, wherein the anion exchange chromatography in step (b) is performed at a pH of 5.0-6.0 and a flow rate of 95-145 cm/hr, and a fraction not attached to the column of anion exchange chromatography is obtained with 1.6-2.0 loading volumes (LV).

5. The method of claim 1, wherein the solvent in step (c) is tri-n-butyl phosphate (TNBP), and the detergent is at least one selected from the group consisting of polysorbate 80, Triton X-100 and Triton X-45.

6. The method of claim 1, wherein the cation-exchange chromatography in step (c) is performed at a pH of 4.5-5.5 and a flow rate of 110-130 cm/hr.

7. The method of claim 1, wherein an adsorption amount of immunoglobulin adsorbed into the cation-exchange resin is 90-130 mg per ml of the cation-exchange resin in the cation-exchange chromatography in step (c).

8. The method of claim 1, wherein the cation-exchange chromatography in step (c) uses a ceramic-based cation exchange resin.

9. The method of claim 1, wherein the dialysis and/or concentration in step (d) is performed using an ultrafiltration/diafiltration (UF/DF) system at an osmotic pressure of 10 mOsmol/kg or lower, and then adjusting pH to 5.5-6.5.

10. The method of claim 1, wherein the anion exchange chromatography in step (d) is performed at a pH of 5.5-6.5 and a flow rate of 90-150 cm/hr, and a fraction not attached to the column of the anion exchange chromatography is obtained with 0.8-1.2 loading volumes (LV).

11. The method of claim 1, wherein in step (d), the pH of the fraction not attached to the column of anion exchange chromatography is adjusted to 4.0-5.5.

12. The method of claim 1, wherein the filtration in step (e) is performed using a nanofiltration or ultrafiltration/diafiltration system.

13. The method of claim 12, wherein the nanofiltration is performed at a pressure of 2.0-3.0 bar, and the ultrafiltration/diafiltration is performed at an osmotic pressure of 10 mOsmol/kg or lower, and then the pH is adjusted to 4.5-5.5.

14. The method of claim 1, further comprising a step of adding a stabilizer to prepare an immunoglobulin for intravenous injection after step (e).

15. The method of claim 14, wherein the stabilizer is at least one selected from the group consisting of sugar alcohol, maltose, sorbitol, mannose, glucose, trehalose, albumin, lysine, glycine, PEG and Tween 80.

16. The method of claim 14, wherein the stabilizer is added to a concentration of 200-300 mM.

17. The method of claim 14, wherein pH of the immunoglobulin solution is adjusted to 4.5-5.5, after addition of the stabilizer.

* * * * *